United States Patent [19]

Feier et al.

[11] 4,314,346

[45] Feb. 2, 1982

[54] AUXILIARY APPARATUS FOR A PARTICLE ANALYSER

[75] Inventors: Markus Feier, Regensdorf; Raymond Frey; Ulrich Marti, both of Zurich, all of Switzerland

[73] Assignee: Contraves AG, Zurich, Switzerland

[21] Appl. No.: 128,643

[22] Filed: Mar. 10, 1980

[30] Foreign Application Priority Data

Mar. 27, 1979 [CH] Switzerland .................. 2824/79

[51] Int. Cl.³ .............................................. G01N 15/02
[52] U.S. Cl. ................................ 364/555; 364/416; 235/92 PC; 324/71 CP
[58] Field of Search .............. 364/555, 416; 324/71 CP; 235/92 PC

[56] References Cited

U.S. PATENT DOCUMENTS

| | | | |
|---|---|---|---|
| 3,557,352 | 1/1971 | Hogg et al. | 364/554 X |
| 3,638,227 | 1/1972 | Angel | 324/71 CP X |
| 3,670,150 | 6/1972 | Hogg | 364/555 X |
| 3,878,369 | 4/1975 | Gahwiler | 324/71 CP X |
| 3,902,053 | 8/1975 | Figueroa | 364/555 |
| 3,936,666 | 2/1976 | Hogg et al. | 364/555 X |
| 3,973,189 | 8/1976 | Angel et al. | 364/416 X |
| 4,021,117 | 5/1977 | Gohde et al. | 364/555 X |
| 4,093,849 | 6/1978 | Baxter, Jr. et al. | 364/416 X |

*Primary Examiner*—Edward J. Wise
*Attorney, Agent, or Firm*—Werner W. Kleeman

[57] ABSTRACT

An auxiliary apparatus for a particle analyzer for measuring the particle count within particle size intervals bounded by shiftable or displaceable thresholds. Infeed lines conduct the signals generated in a feeler to comparators. Other infeed lines conduct the comparison voltages generated by comparison voltage generators to the same comparators, an operating element simultaneously alters the comparison voltages from two comparison voltage generators by the same magnitude and a selector switch connects one of two infeed lines with one of the infeed lines. The inputs of an antivalence or Exclusive-Or discriminator are connected by an infeed line or conductor with a time-delay element and by an infeed line or conductor with one comparator, the output of which discriminator is connected by a line or conductor with a pulse counter.

1 Claim, 4 Drawing Figures

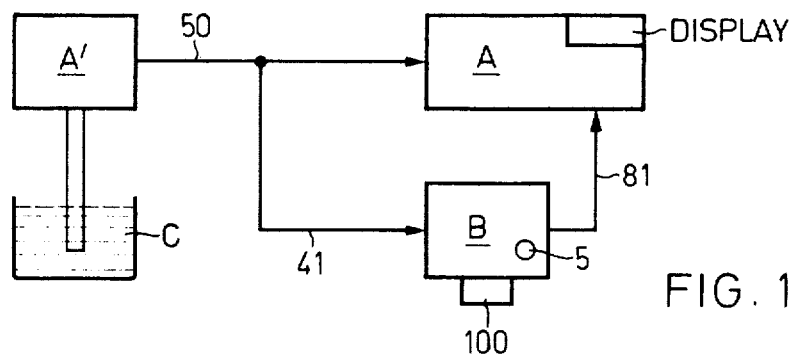
FIG. 1
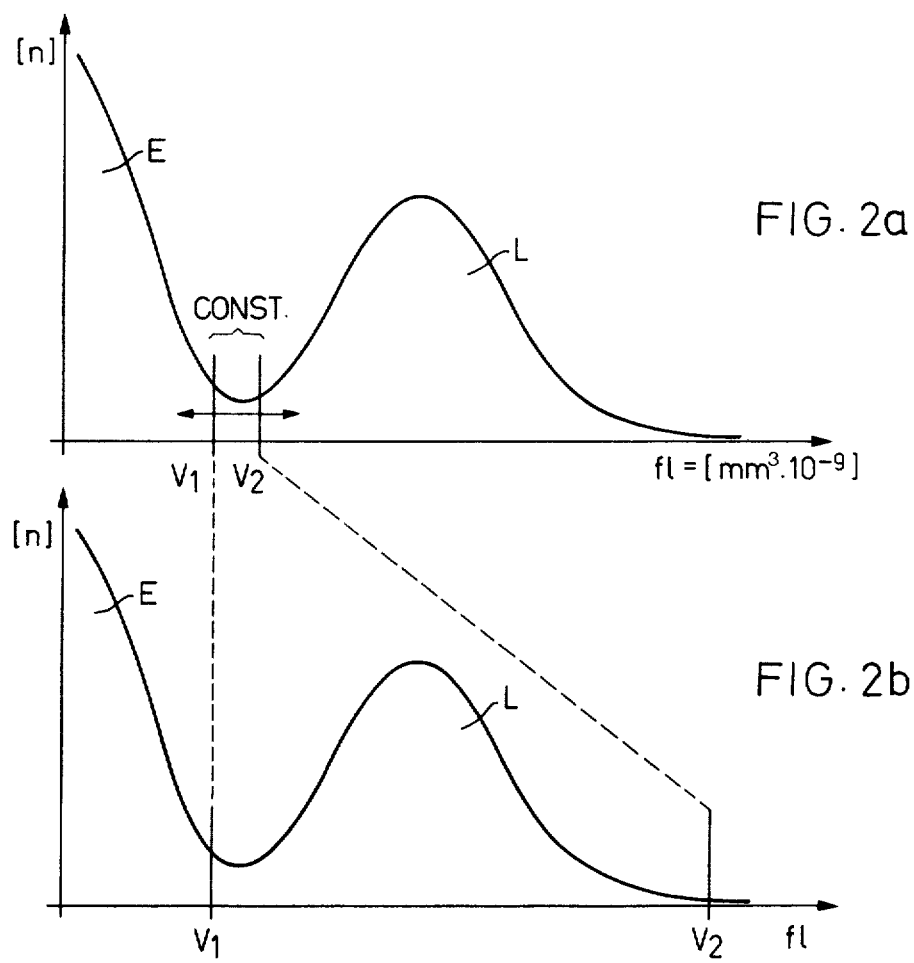
FIG. 2a
FIG. 2b

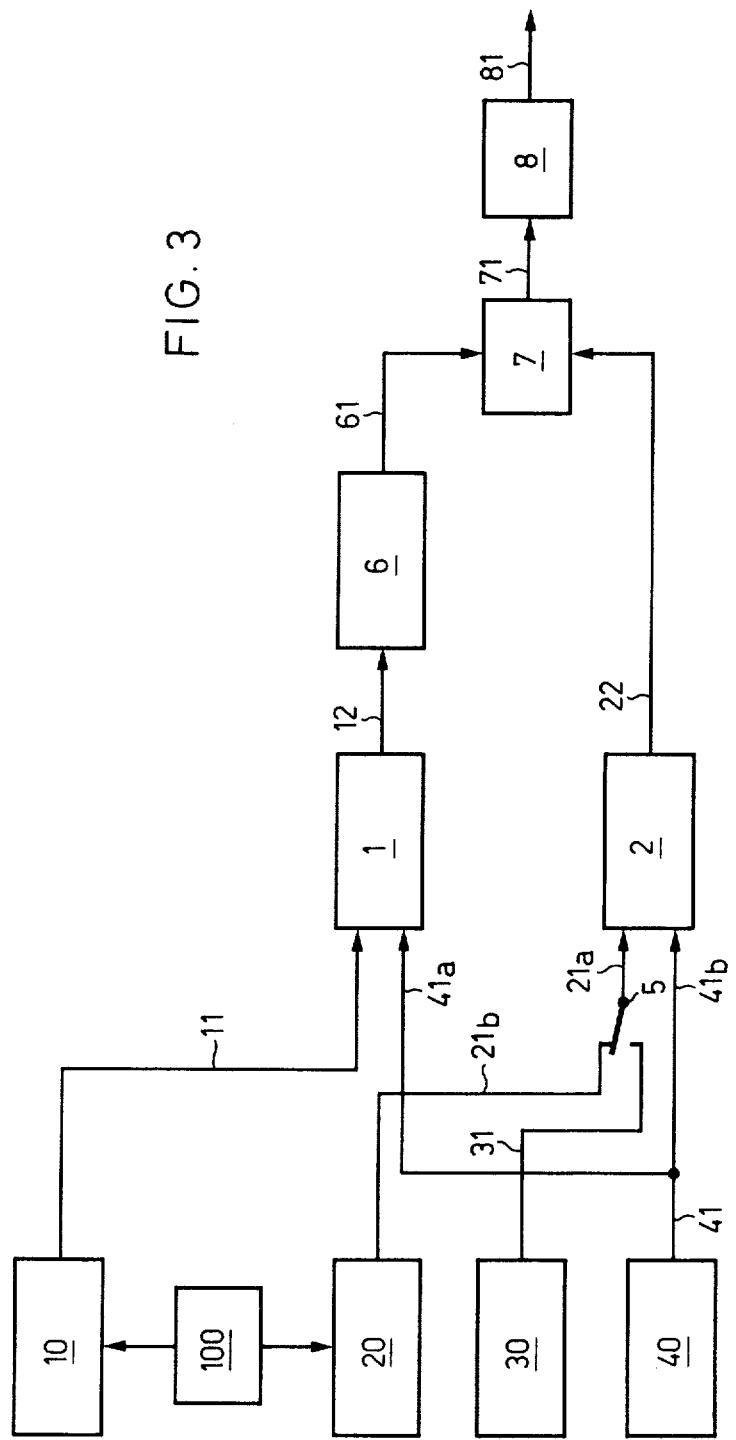

AUXILIARY APPARATUS FOR A PARTICLE ANALYSER

CROSS-REFERENCE TO RELATED CASES

This application is related to U.S. Pat. No. 3,878,369, U.S. patent application Ser. No. 10,963, filed Feb. 9, 1979, now U.S. Pat. No. 4,206,504, granted June 3, 1980, and U.S. patent application Ser. No. 099,646, filed Dec. 3, 1979.

BACKGROUND OF THE INVENTION

The present invention relates to a new and improved construction of an auxiliary apparatus for a particle analyser for measuring the particle count within particle size intervals which are bounded by displaceable or shiftable thresholds, and particularly relates to a particle analyser for the analysis of blood particles, wherein the particle analyser is equipped with feeler means or feelers which generate an electrical signal corresponding to the size of the sensed particles.

It is extremely problematic to analyse a mixture of particles of different size depending upon the distribution of the prevailing classes. What is meant herein by the expression distribution as used in this disclosure, is a discrete distribution of body volume and, in the narrower sense, a histogram of the frequency of the body volumes. In the statistical sense the histogram or the distribution is the probability density that a feature or characteristic, as to its value, will lie within a predetermined interval. The characteristics or features can be of different nature, for instance physical, chemical, morphological and others. If interest is only expressed in the particle count of a certain class, which ideally is present isolated from the distribution of other classes, then the analysis is unambiguous. Prevailing errors usually are attributable to the employed equipment and the accuracy is only limited by the signal-to-noise ratio inherent to the employed system. However, as soon as there are present mixed or hybrid distributions, wherein, for instance, the same size particles of different particle species or classes belong to a respective inherent distribution density, then there are required criteria for discriminating between the overlapping distributions.

With the heretofore known particle analysis equipment there are employed the human efforts of the operator in order to separate certain ranges of a mixed distribution of the body volume. The operator evaluates the distribution spectrum, which is rendered visible in an appropriate and therefore here not further described manner, or a function derived therefrom, and based upon criteria which the operator selects determines a "separation threshold," below which, for instance, the particles are allocated in accordance with their size to one class and above which the particles are then allocated to the other class. The once selected threshold is impressed upon the system, the particle analyser then only detects, for instance, the signals related to the particles which are below or above this threshold. Assuming the signals below the threshold are predicated upon spurious particles, the signals above the threshold upon particles which must be analysed, then the set threshold constitutes a discriminator for spurious and useful signals. If there are measured distributions of a number of size classes, then there must be selected a correspondingly greater number of separation thresholds which must be impressed upon the measuring system, provided that the individual classes are satisfactoriy separated in order to be even able to detect a mixed distribution. This also is true for a bimodal mixed distribution.

Now if a particle analyser is employed for a special purpose, in other words for a limited field of application, say, for blood particle analysis, then for certain equipment designs the thresholds are fixed and cannot be set by external manipulations, in order to separate the particles which should be counted or measured from the particles which should not be incorporated into the measurement.

The setting of separation thresholds in a multimodal distribution curve, in the first instance leads to truncated distributions. The degree of truncation has a direct influence upon the integral over the distribution density, for instance upon the result of a count, and determines, usually dominantly, its accuracy. This is only valid if one stays with the truncated distribution without adequately correcting the same. If the distribution curve changes at the region of a fixed threshold, then by virtue of the increasing or decreasing truncation of the distribution to be analysed there is also altered the result of the analysis. While with prior faulty placement of the separation threshold it is possible for the result to become more accurate, normally however the opposite is true; the obtained result becomes poorer because the threshold previously usually was optimumly set. If, for instance, a particle analyser is designed for volume distribution analysis and for counting erythrocytes in human blood, that is to say, all of the sampled signals emanating from particles of a predetermined particle size interval should contribute to the measurement and a separation threshold should eliminate from the measurement those signals predicated upon artifacts, in other words, particles which are not erythrocytes, then this analyser, apart from possible exceptions, cannot be used, without correction of the threshold, for the counting of erythrocytes in animal blood. If the signal-to-noise ratio of the particle analyser is insufficient, then already the physiologically possible variation range of the cell sizes in human blood requires an individual accommodation of the threshold to each individual blood sample. Such analyser cannot be used at all for the analysis of just any random particles.

There will be clearly recognized from the foregoing the extremely narrow range of application with respect to a distribution function and, additionally, with insufficient signal-to-noise ratio the critical behavior of a particle analyser with separation thresholds which are fixedly set within the circuit design.

It is possible to construct particle analysers in such a manner that the operator, as required, can set the separation threshold or thresholds with the aid of a device mounted externally of the equipment. What previously was the task of an operator who was specially trained, now must be accomplished in equally exact and good quality by the particular random user of the equipment. The so-called setting or adjustment instructions should enable positive "setting" of a desired separation threshold by the user, without such manipulations falsifying the analysis results. Such setting instructions frequently are very simple, but, on the other hand, performance thereof is difficult and unreliable.

Thus, the threshold positioning or setting with the aid of an oscilloscope, where the particle signals in relation to the base noise of the artifacts are visible and can be approximately separated by varying a discriminator or threshold, delivers poorly reproducible values. Another recommended procedure requires the determination of a summation distribution curve. This is obtained by plotting counting results as a function of the threshold position. In the ideal case there is formed a horizontal segment, the so-called plateau, on the basis of which there can be set the threshold. The less the segment or plateau deviates from the horizontal and the greater its range, that much greater is the signal-to-noise ratio of the analyser. In the practical fields of application of blood particle analysis the plateau however, does not have any horizontal section and is also narrowly limited in range. Positioning of the threshold on the basis of the determined curve is unreliable. Furthermore, there must be considered the quite appreciable expenditure in time for the determination of the summation distribution curve, considering the fact that it must be plotted periodically and separately for erythrocytes and leucocytes. Additionally, the cell suspensions which are to be analysed are frequently unstable, something not known to many users. Consequently, the summation distribution curve is falsified and the threshold positioning based thereon is questionable. A possible solution from this dilemma is to improve the signal-to-noise ratio of the analysis system; with a higher investment in sensors and electronic hardware it is possible to obtain a subcritical threshold positioning. A further possibility is to carry out the threshold setting according to the present invention.

In U.S. Pat. No. 3,638,227, granted Jan. 25, 1972, there is disclosed a plotter apparatus which automatically plots the particle count rate as a function of the threshold voltage. Based upon the obtained curves there are set the thresholds in accordance with qualitative criteria, leading to values which are poorly reproducible and dependent upon the dexterity of the operator.

In U.S. Pat. No. 3,557,352, granted Jan. 19, 1971, there is disclosed an auxiliary apparatus for a particle counting system, which determines, by conversion of signals of such system, a particle size which divides the examined system into two parts or fractions which have a certain relationship to one another. For instance, there can be found a mean value of a mass distribution. Yet, the invention disclosed therein does not provide any teaching for finding the minimum between two neighboring classes and such also would not be obvious to one skilled in the art.

In French Pat. No. 2,097,763 there is disclosed a system for receiving optical signals and for the evaluation thereof by a computer system. In particular, within an existing histogram there are detected those signals belonging to a certain class. The field of application of such invention is related to the automatic navigation of space ships. Utilization of this complex system, which has been particularly developed for the processing of optical signals, at an auxiliary device, which would be economical and capable of being fabricated in series, equally would not be obvious for one skilled in the art.

SUMMARY OF THE INVENTION

It is a primary object of the present invention to provide a new and improved construction of an auxiliary apparatus for a particle analyser, by means of which there can be eliminated the uncertainties during threshold setting and with which additionally there can be at least prepared counting of a body volume distribution which is to be examined by limiting or bounding the distribution, so that the conventional error sources are eliminated, which arise by false measurement of the distribution, differences in judgment during the selection of the threshold and due to imprecise setting of the selected threshold.

In keeping with the immediately preceding objective the novel auxiliary apparatus further enables maintaining the measuring integrity, and thus, the analysis accuracy, even when the equipment is operated by less skilled users.

Now in order to implement these and still further objects of the invention, which will become more readily apparent as the description proceeds, the invention provides an auxiliary apparatus for a particle analyser for measuring the particle count within particle size intervals limited by displaceable thresholds, especially for a particle analyser for the analysis of blood particles, wherein the particle analyser is equipped with feeler or sensor means which generate an electrical signal corresponding to the size of the sensed particles. According to the invention there is provided a first comparator having an infeed line for the electrical signal received from a feeler element and a second infeed line for receiving a first comparison voltage from means for generating such comparison voltage. A second comparator has an infeed line for the electrical signal received from the feeler element or feeler and has a further infeed line for receiving a second comparison voltage from means for generating this second comparison voltage. Means serve for simultaneously changing the first and second comparison voltages by the same magnitude or amount, and means serve to generate a third comparison voltage. Switch means are arranged at the infeed lines of the second comparison voltage leading to the second comparator for switching to an infeed line leading from the means for generating the third comparison voltage. There are also provided means for delaying the output signal at the line leading from the first comparator, and means for discriminating an antivalence and having an infeed line leading from the time-delay element and a further infeed line leading from the second comparator. A pulse counter is provided having an infeed line leading from the antivalence discriminator.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 illustrates the coaction of the auxiliary apparatus with a particle counter and the sample solution which is to be measured;

FIG. 2a illustrates a bimodal size distribution of the particles with two discriminator thresholds $V_1$ and $V_2$ at the transition region of two particle classes;

FIG. 2b shows the distribution of FIG. 2a with shifted discriminator threshold $V_2$ for the detection of a particle class; and FIG. 3 is a block circuit diagram of the auxiliary apparatus.

DETAILED DESCRIPTION OF THE PREFERRED EMBODIMENTS

Describing now the drawings, for the analysis an appropriately prepared sample of a liquid containing erythrocytes and leucocytes is conducted through a feeling or scanning zone, wherein the feeler or scanner means can be designed for instance to be electrical or optical in nature. The particles suspended in the liquid are scanned during their passage through the scanning zone, and the scanned particles generate suitable pulses or signals of different characteristics or properties as a function of the physical characteristics of the sampled particle types.

During the analysis of leucocytes the advantageous preparation of the sample, among other things, resides in removing the erythrocytes by means of hemolysis and which erythrocytes are typically present in a 1000-fold higher concentration. During this treatment the erythrocytes are specifically destroyed and there is now present in the solution to be examined a many thousand-fold higher concentration of cell fragments of the destroyed erythrocytes in relation to the morphologically altered but intact leucocytes. These fragments form, or should form, a different size class than the leucocytes; coarsely considered there is present a bimodal mixed distribution. In the ideal case the distribution of the artifacts, in this instance the fragment particles, is well separated from the distribution of the leucocytes and a separation of both distributions by a separation threshold leads to a truncated distribution of the leucocytes with an extremely small degree of truncation; a subsequent correction therefore can be dispensed with.

Practical experience has shown that results from an uncorrected, truncated distribution are also usable with markedly overlapping mixed distributions. Thus, for instance, during erythrocyte analysis, the deviation from an approximate normal distribution constitutes evidence as to a certain pathological change and in graphical portrayal can be used as a further result of the analysis. The consequence of this is that: classes having marked deviation from the normal distribution cannot be positively corrected even when incorporating into the analysis usually complicated computation procedures. The result from a truncated distribution together with a quality criterion, for instance the amplitude of the threshold value, is easier to judge than an inadequately corrected result. Thus, in practice, there is normally dispensed with a correction of the truncated distribution.

In FIG. 1 there is shown a block diagram of a particle counter A with the related feeler or sensor element A', which for ease in illustration has been shown immersed in a particle sample C which is to be examined. The signal line 50 between the feeler element A' and the particle counter A is tapped-off by the infeed line 41 leading to the auxiliary apparatus B, in order to infeed the electrical particle signals to such auxiliary apparatus B. An operating device 100 allows performance of the requisite manipulations for setting the desired threshold. The particles in the range of the threshold are counted and the counting result is infed by means of the infeed line 81 for further evaluation to the particle analyser A. Of course, the auxiliary apparatus B can be physically incorporated within the particle counter A, so that several of the components illustrated in FIG. 3 perform a dual function. For instance, the pulses appearing at the line 71 (FIG. 3) can be infed to a pulse counter located in the particle analyser. A switching device 5 at the auxiliary apparatus B (FIG. 1) enables, as a further operating element, switching from the operating mode "finding thresold" to the operating mode "particle counting," under which there is meant the counting and display of a particle class which is to be entirely determined. The operation of the operating device 100 has been shown in FIG. 2a and the operation of the switching device 5 in FIG. 2b.

FIG. 2a illustrates a typical bimodal size class distribution having a relatively clearly discernible or pronounced transition from one size class to the other. Related to the example of leucocyte analysis, the not completely illustrated distribution of the class E is predicated upon the hemolyzed erythrocytes, in other words their fragments, while the distribution of the class L is predicated upon the intact leucocytes. The cell fragments of the erythrocytes as particles, intentionally, form a class having a mean value of the particle size which is clearly smaller than the mean value of the intact leucocytes. Thus, the artifacts (erythrocyte fragments) can be separated from the leucocytes where are to be analysed by setting a threshold.

The threshold value is now set at the lowest point in the valley between both classes. As already previously explained, this is accomplished either in indirect form by means of a summation distribution curve or in direct form with the aid of an oscilloscope, in the latter case without counting, predicated upon a visual impression of a minimum pulse count of those pulses which project past the simultaneously displayed pulses of the "artifact noise."

It is well known that a human being is most capable of determining the number of elements of a quantity when such are present in an explicit form (for instance the human can readily imagine the quantitative value for instance in the form of a value such as 500 screws per box). The invention proceeds from this recognition and delivers for the separation threshold a numerical value instead of the heretofore usual diagrammatic portrayal.

According to FIG. 2a and also FIG. 2b the particle quantity per volume unit of the sample at the valley between both distributions, in other words between both of the thresholds $V_1$ and $V_2$, is smallest. Now if by means of the selector switch or reversing switch means 5 the difference $V_2 - V_1$ is made very small, i.e. the particle size range should be small, which here corresponds to the positions of FIG. 2a, and thereafter with the aid of the operating device 100 the thresholds $V_1$ and $V_2$ are simultaneously shifted or displaced over the particle volume range—indicated by a double-headed arrow—, then it is possible to perform at arbitrarily chosen positions a brief particle counting of volumes which each time are of equal size; the determined count is directly indicated in a display. This corresponds to the explicit representation of the counted elements of a quantity. In practice for such type counting there is needed only a few seconds. By systematically shifting and counting in the direction of smaller count values there is determined the valley base extremely quickly, positively and with very slight observation expenditure on the part of the operator, i.e., the location where the fault due to truncation is lowest. With increasing experience in handling the auxiliary apparatus it is possible to observe the count rate (particle/time unit) while shifting the threshold pairs $V_1$, $V_2$ during the counting operation; in this way it is possible to further reduce the time needed for finding a threshold.

Thereafter, by means of the reversing switch means or selector switch 5 the threshold $V_2$ is shifted through such a magnitude that, as determined by empirical values or experience, it encompasses the distribution of the leucocytes (FIG. 2b) and there can be carried out an analysis count. For improved clarity in illustration both of the thresholds $V_1$ and $V_2$ have been shown in FIG. 2a spaced unrealistically far apart from one another, and for this reason also the lower discriminating threshold $V_1$ in FIG. 2b appears to be shifted into the artifact region. If there is desired, for instance, a further increased accuracy of the threshold position, then by means of an additional switch contact in the line or conductor leading to the first comparator it is possible, by means of a further comparison voltage, to shift the threshold $V_1$—simultaneous with the shifting of the threshold value $V_2$—by the half magnitude $V_2-V_1$ in the direction of greater particle volume sizes.

If the threshold has once been set at the start of an analytical measurement series, then during each new measurement of blood samples of the same species, it is possible to determine within seconds whether the threshold has been placed at the proper position or whether there is required a correction. As a further auxiliary means or aid for setting the threshold at the start of a measuring series with unknown distribution it has been found to be advantageous to use a simultaneous acoustical indicator, for instance a small loudspeaker, during the systematic displacement or shifting of the threshold pair in the direction of lower counting values. The effect is similar to that encountered with a Geiger counter, there is produced an integral impression of the quantity of the particle pulses and together with the explicit quantity display or indication there is obtained a redundancy which is favorable for the measurement reliability. The already mentioned minimization of the counting rate is further facilitated with the aid of this acoustical indicator.

Finally, in FIG. 3 there is shown in block circuit diagram the interconnection of the different circuit components, which components are conventional and thus need not be described here in detail they are well known in the electronics art. By referring to FIG. 3 there will be recognized a first comparator 1 having an infeed line or conductor 41a leading from a feeler or sensor element 40 and receiving the electrical signals which are generated by such feeler element 40. The comparator 1 also is provided with an infeed line 11 carrying a first comparison voltage or potential which is produced by the means 10 for generating such first comparison voltage. There is also provided a second comparator 2 having an infeed line 41b connected with the feeler 40 for receiving the electrical signal generated by the feeler or feeler element 40. The comparator 2 also has further infeed lines or conductors 21a, 21b which receive a second comparison voltage or potential from the means 20 which generate such second comparison voltage. There are also provided means 100 for the simultaneous variation of the first comparison voltage and the second comparison voltage by the same amount or magnitude, and means 30 for generating a third comparison voltage. A switch or reversing switch means 5 is arranged at the infeed lines or conductors 21a, 21b carrying the second comparison voltage and leading to the second comparator 2 for switching to the infeed lines or conductors 31, 21a leading from the means 30 which generate the third comparison voltage. Reference character 6 designates means for delaying the output signal appearing at the line or conductor 12 at the output side of the first comparator 1, and reference character 7 constitutes an antivalence discriminator means having an infeed line or conductor 61 leading from the time-delay element or means 6 and a further infeed line or conductor 22 leading from the second comparator 2. Finally, there is provided a pulse counter 8 having an infeed line or conductor 71 leading from the output side of the antivalence or Exclusive-Or discriminator 7.

While there are shown and described present preferred embodiments of the invention, it is to be distinctly understood that the invention is not limited thereto, but may be otherwise variously embodied and practiced within the scope of the following claims. Accordingly,

What we claim is:

1. In an auxiliary apparatus for a particle analyser for measuring the particle count within particle size intervals limited by displaceable thresholds, especially for a particle analyser for the analysis of blood particles, wherein the particle analyser is equipped with feeler means generating an electrical signal corresponding to the size of the sensed particles, the improvement of which comprises:

feeler means for generating an electrical signal corresponding to the size of the sensed particles;

a first comparator;

an infeed line for connecting said feeler means with said first comparator for the infeed of the electrical signals generated by the feeler means to said first comparator;

means for generating a first comparison voltage;

an infeed line for said first comparator for infeeding the first comparison voltage from said means generating said first comparison voltage to said first comparator;

a second comparator;

an infeed line leading from said feeler means to said second comparator for infeeding the electrical signals generated by said feeler means to said second comparator;

means for generating a second comparator voltage and having an output line means;

an infeed line leading to said second comparator for infeeding the second comparison voltage from said means generating said second comparison voltage to said second comparator;

voltage shifting means for simultaneously altering the first comparison voltage and the second comparison voltage by the same amount;

means for generating a third comparison voltage and having an output line means;

infeed line means provided for said second comparator;

reversing switch means for selectively connecting either the output line means of said means for generating a second comparison voltage or the output line means of said means for generating a third comparison voltage to the infeed line means provided for said second comparator;

said first comparator having an output side;

time-delay means containing an infeed line connected with the output side of said first comparator for delaying the output signal appearing at said infeed line leading from said first comparator to said time-delay means;

said time-delay means having an output side;

antivalence discriminator means connected by an infeed line with the output side of said time-delay means;

a further infeed line leading from the second comparator to said antivalence discriminator means;

said antivalence discriminator means having an output side; and pulse counter means connected by an infeed line with the output side of said antivalence discriminator means.

* * * * *